United States Patent
Müller

(10) Patent No.: US 6,540,661 B1
(45) Date of Patent: Apr. 1, 2003

(54) ARRANGEMENT FOR COUPLING OF A DRIVER TO A COUPLING SITE OF THE OSSICULAR CHAIN

(75) Inventor: Gerd M. Müller, Lohhof (DE)

(73) Assignee: Phonak AG, Stafa (CH)

( * ) Notice: Subject to any disclaimer, the term of this patent is extended or adjusted under 35 U.S.C. 154(b) by 91 days.

(21) Appl. No.: 09/680,489

(22) Filed: Oct. 6, 2000

(30) Foreign Application Priority Data

Oct. 7, 1999 (DE) .......................... 199 48 336

(51) Int. Cl.$^7$ .............................. H04R 25/00
(52) U.S. Cl. ...................................... 600/25
(58) Field of Search .............. 600/25; 607/55, 607/56, 57, 136, 137; 381/68; 181/128, 129

(56) References Cited

U.S. PATENT DOCUMENTS

| | | |
|---|---|---|
| 3,712,962 A | 1/1973 | Epley |
| 3,870,832 A | 3/1975 | Fredrickson |
| 3,882,285 A | 5/1975 | Nunley et al. |
| 4,850,962 A | 7/1989 | Schaefer |
| 5,015,224 A | 5/1991 | Maniglia |
| 5,015,225 A | 5/1991 | Hough et al. |
| 5,277,694 A | 1/1994 | Leysieffer et al. |
| 5,370,689 A | 12/1994 | Causse |
| 5,554,096 A | 9/1996 | Ball |
| 5,624,376 A | 4/1997 | Ball et al. |
| 5,707,338 A | 1/1998 | Adams et al. |
| 5,788,711 A | 8/1998 | Lehner et al. |
| 5,941,814 A | 8/1999 | Lehner et al. |
| 5,954,628 A | 9/1999 | Kennedy |
| 6,077,215 A | 6/2000 | Leysieffer |

FOREIGN PATENT DOCUMENTS

| | | |
|---|---|---|
| WO | WO 98/06235 | 2/1998 |
| WO | WO 98/06236 | 2/1998 |
| WO | WO 98/06237 | 2/1998 |
| WO | WO 98/06238 | 2/1998 |
| WO | WO 99/08475 | 2/1999 |

OTHER PUBLICATIONS

H.P. Zenner, Et Al., Active Electronic Hearing Implants for Labyrinthine and Conduction Deafness—A New Era of Ear Surgery, HNO 1997—vol. 45, Oct. 1997, pp. 749–774.

H. Leysieffer Et Al., An Implantable Piezoelectric Hearing Aid Converter for Patients with Labyrinthine Deafness, HNO 1997—vol. 45, Oct. 1997, pp. 792–800.

H. Leysieffer Et Al., Ein Vollständig Implantierbares Hoörsystem Für Innenohrschwerhörige: TICA LZ 3001, HNO 1998, vol. 46, Oct. 1998, pp. 853–863.

(List continued on next page.)

Primary Examiner—Max F. Hindenburg
Assistant Examiner—Brian Szmal
(74) Attorney, Agent, or Firm—Nixon Peabody LLP; David S. Safran

(57) ABSTRACT

A mechanical coupling for an output-side driver of an active or passive implantable hearing system. The driver is adapted to vibrate a preselected coupling site on an ossicular chain via a first coupling which has a coupling rod which can be caused to vibrate mechanically by the driver and a coupling element which can be connected to the preselected coupling site. The coupling rod and the coupling element are interconnected by at least one coupling. A first coupling half of the coupling has an approximately spherical outside contour which can be accommodated in the inside contour of a second coupling half, i.e. a contour which is at least partially complementary to the outside contour. The is adapted to reversibly swivel and/or turn against friction forces, but is essentially rigid under the dynamic forces which occur in the implanted state.

24 Claims, 7 Drawing Sheets

OTHER PUBLICATIONS

H.P. Zenner Et Al., Erste Implantationen Eines Vollständig Implantierbaren Elektronischen Hörsystems Bei Patienten Mit Innenohr–Schwerhörigkeit, HNO 1998, vol. 46, Oct. 1998, pp. 844–852.

Anthony J. Maniglia Et Al., Contactless Semi–Imlantable Electromagnetic Middle Ear Device for the Treatment of Sensorineural Hearing Loss, vol. 28, No. 1, Feb. 1995, pp. 121–141.

John M. Fredrickson Et Al., Ongoing Investigations into an Implantable Electromagnetic Hearing Aid for Moderate to Severe Sensorineural Hearing Loss, vol. 28, No. 1, Feb. 1995, pp. 107–121.

Naoaki Yanagihara Et Al., Efficacy of the Partially Implantable Middle Ear Implant in Middle and Inner Ear Disorders, Adv. Audiol., vol. 4, Karger, Basel 1988, pp. 149–159.

Jun–Ichi Suzuki Et Al., Implantation of Partially Implantable Middle Ear Implant and the Indication, Adv. Audiol., vol. 4, Karger, Basel 1988, pp. 160–166.

Dennis I. Bojrab, MD, Et Al., Ossiculoplasty with Composite Prostheses, Otolaryngologic Clinics of North America, vol. 27, No. 4, Aug. 1994.

R. Lehner Et Al., Cold–Flowing Elements for Coupling of an Implantable Hearing Aid Converter to Auditory Ossicle or Perilymph, HNO 1998—vol. 46, Jan. 1998, pp. 27–37.

Patent Abstracts of Japan, Publication No. 11196498 A, Jul. 21, 1999, Satou Kumiko, Hearing Aid, English Abstract.

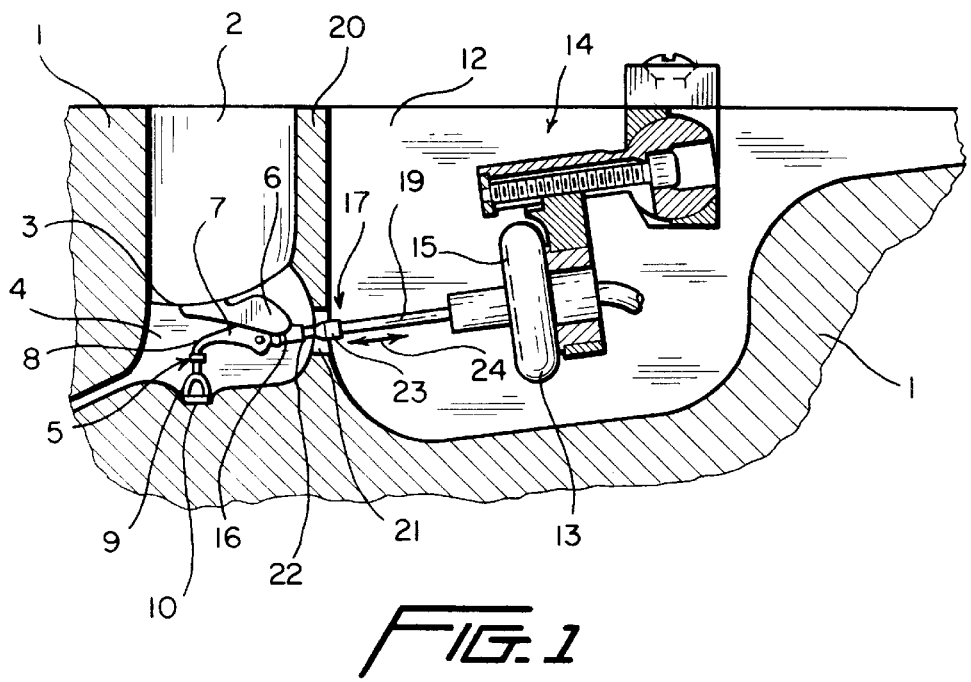
FIG. 1
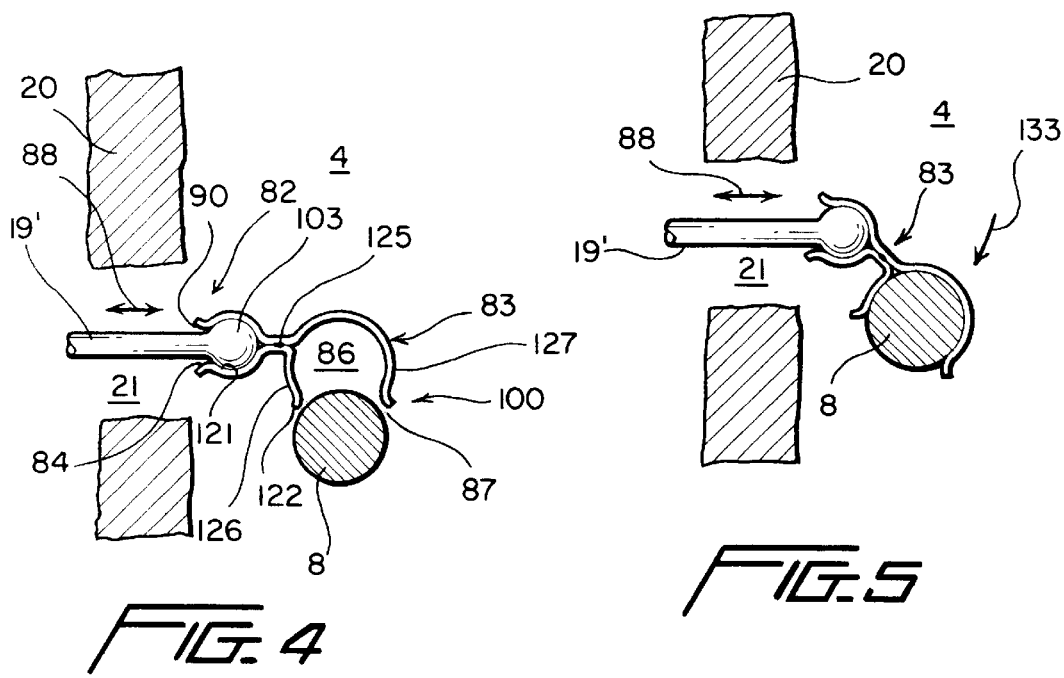
FIG. 4
FIG. 5

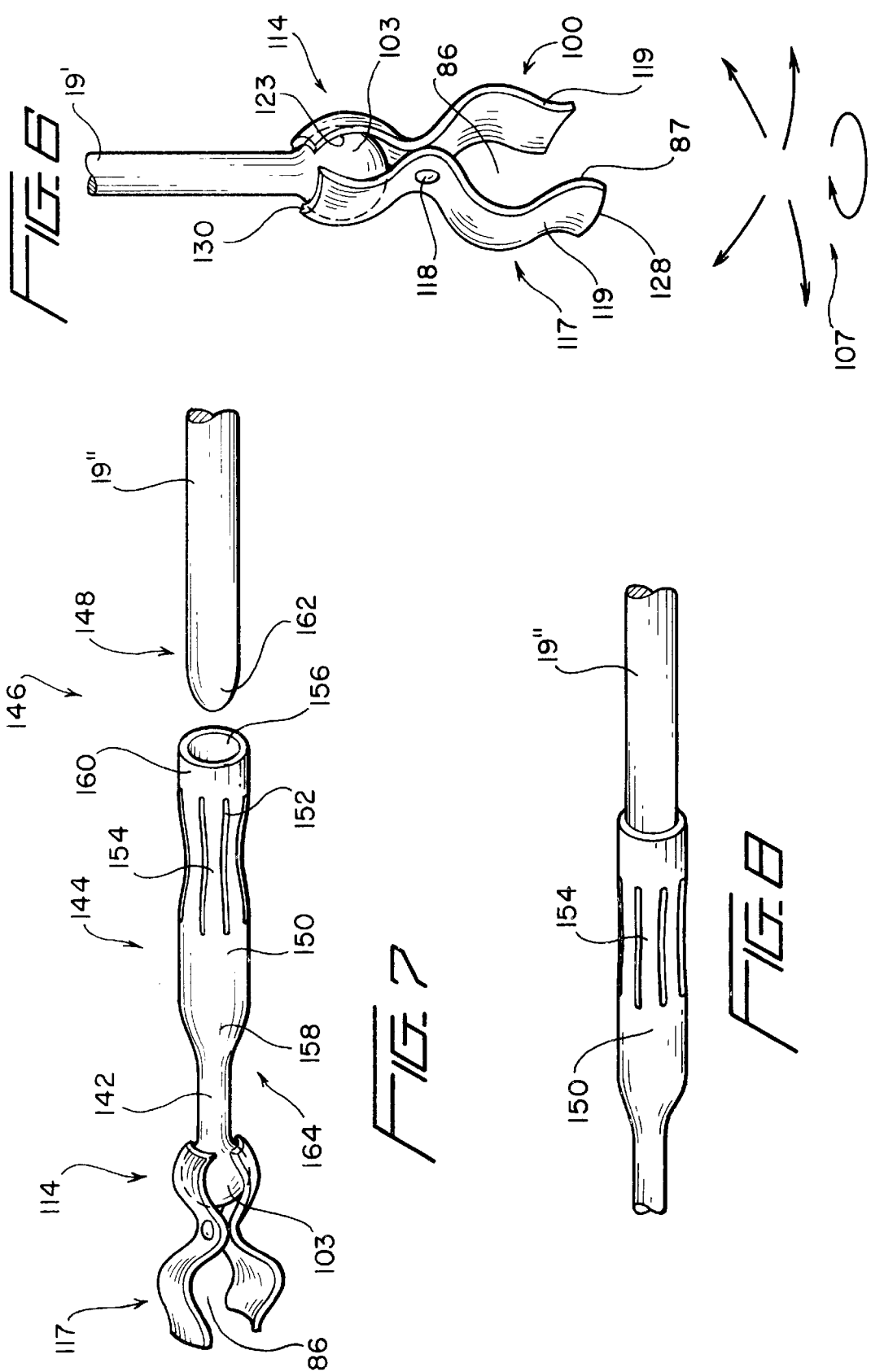

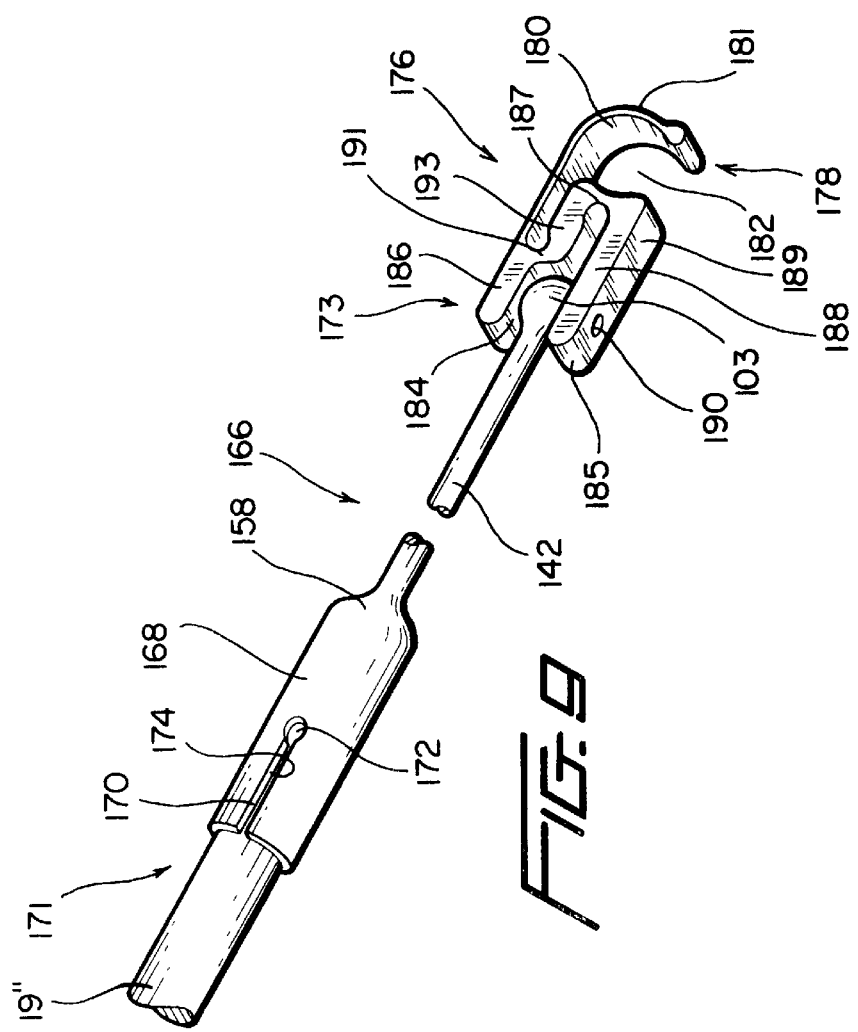
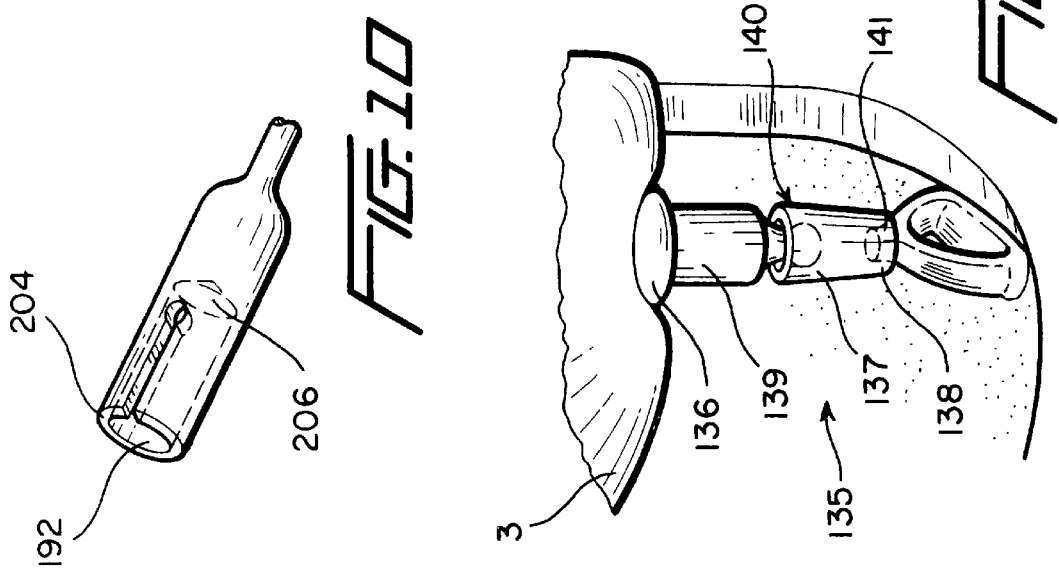

ARRANGEMENT FOR COUPLING OF A DRIVER TO A COUPLING SITE OF THE OSSICULAR CHAIN

BACKGROUND OF THE INVENTION

1. Field of the Invention

The invention relates to an implantable arrangement for mechanical coupling of an output-side driver member of an active or passive hearing system, the driver member being adapted to be excited to mechanical vibrations, to a preselected coupling site on the ossicular chain, the footplate of the stapes or a membrane which closes the round window or an artificial window in the cochlea, in the vestibulum or in the labyrinth (equilibrium organ), via a coupling arrangement which has a coupling rod which can be excited to mechanical vibrations by the driver member, and a coupling element which can be connected to said preselected coupling site, the coupling rod and the coupling element being interconnected via at least one coupling and at least a section of the coupling element which in the implanted state contacts the coupling site being designed for vibratory input to the coupling site.

2. Description of Related Art

Partially implantable or fully implantable active hearing systems for direct mechanical stimulation are known. In these hearing systems the acoustic signal is converted into an electrical signal by a converter (microphone) and is amplified in an electronic signal processing unit; this amplified electrical signal is supplied to an implanted electromechanical converter the output-side mechanical vibrations of which are supplied directly, i.e. with direct mechanical contact, to the middle ear or inner ear. This applies regardless of whether pure labyrinthine deafness with a completely intact middle ear or combined deafness (middle ear and inner ear damaged) is to be rehabilitated. Therefore, implantable electromechanical converters and processes for direct coupling of the mechanical converter vibrations to the intact middle ear or to the inner ear for rehabilitation of pure labyrinthine deafness and also to the remaining ossicles of the middle ear in an artificially or pathologically altered middle ear for treatment of conductive deafness and their combinations have been described in the more recent scientific and patent literature.

Basically all physical conversion principles can be used as electromechanical converter processes, such electromagnetic, electrodynamic, magnetostrictive, dielectric, and piezoelectric. In recent years various research groups have focused essentially on two of these processes: electromagnetic and piezoelectric. An outline of these converter versions can be found in Zenner and Leysieffer (HNO 1997, Vol. 45, pp. 749 –774).

In the piezoelectric process, mechanically direct coupling of the output-side converter vibrations to the middle ear ossicle or directly to the oval window is necessary. In the electromagnetic principle, the force coupling, on the one hand, can take place via an air gap ("contactless"), i.e. only a permanent magnet is placed by permanent fixation in direct mechanical contact with a middle ear ossicle. On the other hand, it is possible to dispose the entire converter within a housing (the coil and the magnet being coupled with the smallest possible air gap) and to transfer the output-side vibrations via a mechanically stiff coupling element with direct contact to the middle ear ossicle (Leysieffer et al., HNO 1997, Vol. 45., pp. 792–800).

The patent literature contains some of the aforementioned versions of both electromagnetic and also piezoelectric hearing aid converters: U.S. Pat. No. 5,707,338 (Adams et al.), WO 98/06235 (Adams et al.), WO 98/06238 (Adams et al.), WO 98/06236 (Kroll et al.), WO 98/06237 (Bushek et al.), U.S. Pat. No. 5,554,096 (Ball), U.S. Pat. No. 3,712,962 (Epley), U.S. Pat. No. 3,870,832 (Fredrickson), U.S. Pat. No. 5,277,694 (Leysieffer et al.), published European Patent Application Nos. EP-A-0 984 663 and EP-A-0 984 665 (corresponding to commonly owned U.S. Patent Application Nos. 09/275,872 and 09/311,563, respectively) (Leysieffer), U.S. Pat. No. 5,015,224 (Maniglia), U.S. Pat. No. 3,882,285 (Nunley), and U.S. Pat. No. 4,850,962 (Schaefer).

The partially implantable piezoelectric hearing system of the Japanese group of Suzuki and Yanigahara presupposes for implantation of the converter the absence of the middle ear ossicles and an empty tympanic cavity in order to be able to couple the piezoelement to the stapes (Yanigahara et al.: Efficacy of the partially implantable middle ear implant in middle and inner ear disorders, Adv. Audiol., Vol. 4, Karger Basel (1988), pp. 149–159; Suzuki et al.: Implantation of partially implantable middle ear implant and the indication, Adv. Audiol., Vol. 4, Karger Basel (1988), pp. 160166). Similarly, in the process of an implantable hearing system for those suffering from labyrinthine deafness in accordance with U.S. Pat. No. 4,850,962 (Schaefer), basically, the incus is removed in order to be able to couple a piezoelectric converter element to the stapes. This also applies especially to other developments which are based on the Schaefer technology and which are documented in the aforementioned patents (U.S. Pat. No. 5,707,338, WO 98/06235, WO 98/06238, WO 98/06236, and WO 98/06237).

Conversely, the electromagnetic converter of BALL ("Floating Mass Transducer FMT", U.S. Pat. No. 5,624,376, and U.S. Pat. No. 5,554,096) is fixed with titanium clips directly to the long process of the incus when the middle ear is intact. The electromagnetic converter of the partially implantable system of FREDRICKSON (Fredrickson et al.: Ongoing investigations into an implantable electromagnetic hearing aid for moderate to severe sensorineural hearing loss, Otolaryngologic Clinics of North America, Vol. 28/1 (1995), pp. 107–121) is mechanically coupled directly to the body of the incus when the ossicular chain of the middle ear is likewise intact. The same applies to the piezoelectric and electromagnetic converters of LEYSIEFFER (Leysieffer et al.: An implantable piezoelectric hearing aid converter for patients with labyrinthine deafness, HNO 1997/45, pp. 792–800; U.S. Pat. No. 5,277,694, U.S. Patent Application Nos. 09/275,872 and 09/311,563 (Leysieffer)). Also, in the electromagnetic converter system of MANIGLIA (Maniglia et al: Contactless semi-implantable electromagnetic middle ear device for the treatment of sensorineural hearing loss, Otolaryngologic Clinics of North America, Vol. 28/1 (1995), pp. 121–141), when the ossicular chain, is intact, a permanent magnet is permanently fixed mechanically to the ossicular chain but is, however, mechanically driven via an air gap coupling by a coil.

In the described converter and coupling versions, basically, two implantation principles can be distinguished:

a) On the one hand, the electromechanical converter with its active converter element is located itself in the middle ear region in the tympanic cavity and the converter is directly connected there to an ossicle or the inner ear (U.S. Patent No. 4,850,962, U.S. Pat. No. 5,015,225, U.S. Pat. No. 5,707,338, WO 98/06235, WO 98/06238, WO 98/06236, WO 98/06237, U.S. Pat. No. 5,624,376, and U.S. Patent No. 5,554,096).

b) On the other hand, the electromagnetic converter with its active converter element is located outside of the middle ear region in an artificially formed mastoid cavity. The output-side mechanical vibrations are then transmitted to the middle or inner ear by means of mechanically passive coupling elements via suitable surgical accesses (the natural aditus ad antrum, opening of the chorda-facialis angle or via an artificial hole from the mastoid) (Fredrickson et al.: Ongoing investigations into an implantable electromagnetic hearing aid for moderate to severe sensorineural hearing loss, Otolaryngologic Clinics of North America, Vol. 28/1 (1995), pp. 107–121; U.S. Pat. No. 5,277,694; U.S. patent application Ser. Nos. 09/275,872 and 09/311,563 (Leysieffer)).

In a)-type versions, the converter can be made as a so-called "floating mass"converter, i.e. the converter element does not require any "reaction",via secure screwing to the skull bone, rather it vibrates based on the laws of mass inertia with its converter housing and transmits these vibrations directly to a middle ear ossicle (U.S. Pat. No. 5,624,376, U.S. Pat. No. 5,554,096, U.S. Pat. No. 5,707,338, and WO 98/06236). On the one hand, this means that an implantable fixation system on the cranial vault can be advantageously omitted, and, on the other hand, this version disadvantageously means that bulky artificial elements must be placed in the tympanic cavity, and their long-term stability and biostability are currently not known or guaranteed, especially in the case of temporary pathological changes of the middle ear (for example, otitis media). Another major disadvantage is that the converter together with its electrical supply line has to be transferred from the mastoid into the middle ear and must be fixed there using suitable surgical tools; this requires expanded access through the chorda facialis angle and, thus, entails a latent hazard to the facial nerve which is located in the immediate vicinity.

In the b)-type converter versions, the converter housing with the implantable positioning and fixation systems is attached to the cranial vault (advantageous embodiment U.S. Pat. No. 5,788,711). Both in the partially implantable system of FREDRICKSON (Ongoing investigations into an implantable electromagnetic hearing aid for moderate to severe sensorineural hearing loss, Otolaryngologic Clinics of North America, Vol. 28/1 (1995), pp. 107–121), as well as in the fully implantable hearing system of LEYSIEFFER and ZENNER (HNO 1998, vol. 46, pp. 853–863 and 844–852), when the vibrating driver member is coupled to the body of the incus, it is assumed, for permanent and mechanically secure vibration transmission, that the tip of the coupling rod, which is placed in the laser-induced depression of the middle ear ossicle, undergoes osseointegration over the long term, i.e. the coupling rod coalesces solidly with the ossicle, and thus, ensures reliable transmission of dynamic compressive and tensile forces. This long-term effect, however, is currently not yet scientifically proven or certain. Furthermore, in this type of coupling, in case of a technical converter defect, there is the disadvantage that decoupling from the ossicle to remove the converter can only be done with mechanically based surgical methods; w this can mean considerable hazard to the middle ear and especially the inner ear.

The major advantage of these converter embodiments as per b) however, is that the middle ear remains largely free and coupling access to the middle ear can take place without major possible hazard to the facial nerve. One preferable surgical process for this purpose is described in U.S. Pat. No. 6,077,215. Basic advantageous forms of passive coupling elements for transmission of the output-side converter vibrations from the mastoid to the middle ear or inner ear are described in U.S. Pat. No. 5,277,694; U.S. Pat. No. 5,941,814; and in HNO 1998 Vol. 46, pp. 27–37—Lehner et al.: "Cold-flowing elements for coupling of an implantable hearing aid converter to the auditory ossicle or perilymph". The coupling elements are especially made of gold, preferably, soft-annealed fme gold, in the form of a C-band for the long process of the incus, a band loop for the long process of the incus and a tiny bell for the head of the stapes, and these coupling elements can be coupled using instruments which are standard in ear surgery, and if necessary, they can also be detached again.

Commonly owned U.S. Patent Application No. 09/626,745 (filed on Jul. 26, 2000 and entitled "Arrangement for Mechanical Coupling of a Driver to a Coupling Site of the Ossicular Chain") describes an implantable arrangement for mechanical coupling of an output-side driver member of an active or passive hearing system, the driver member being adapted to be excited to mechanical vibrations to a preselected coupling site on the ossicular chain, the footplate of the stapes or a membrane which closes the round window or an artificial window in the cochlea, in the vestibulum or in the labyrinth (equilibrium organ), via a coupling arrangement which has a coupling element which can be connected to the preselected coupling site. An attenuator element with entropy-elastic properties which, in the implanted state, contacts the coupling site, causes a coupling with low characteristic acoustic impedance and a reduction of the risk of damage to natural structures in the area of the coupling site during and after implantation.

WO 99/08475 discloses an active hearing system in which a capacitive sensor converts vibrations of the malleus into an electrical signal which after passing through an electronic circuit is supplied to a stimulator, which for its part, mechanically or electrically stimulates the inner ear. The capacitive sensor includes a first electrode, which is pivotally coupled to the malleus via a ball joint coupling, and a second electrode, which is either rigidly fixed to the mastoid or is likewise pivotally coupled to the mastoid via a ball joint coupling. The ball joint coupling is designed such that the two electrodes can freely align themselves with respect to one another even if the vibration direction of the malleus changes for example as a function of frequency.

An arrangement is described in U.S. Pat. No. 5,941,814 in which the first coupling half is essentially rod-shaped and the second coupling half is made roughly sleeve-shaped, and by pushing and/or turning the two coupling halves, the relative location of the coupling rod and coupling element can be adjusted in situ at the implantation site. The two components are fixed reliably with long term stability in the set relative position by applying a crimping force, using a crimping tool, to the sleeve-shaped second coupling half, by which the latter is plastically cold-formed, whereas the rod-shaped first coupling half is not subjected to plastic cold-forming under the action of a crimping force.

In addition to the described active hearing systems, passive hearing systems are also known in the form of prostheses as total replacement (T.O.R.P.=total ossicular replacement prosthesis) or as partial replacement (P.O.R.P.=partial ossicular replacement prosthesis) for the ossicular chain (D.I. Bojrab et al. "Ossiculoplasty with composite prostheses",in Otolaryngologic Clinics of North America, Vol. 27, No. 4, 1994, pp. 759–776). In these passive systems the eardrum itself or an area of the still intact "remainder",of the ossicular chain facing the eardrum forms the output-side driver member. Thus, U.S. Pat. No. 5,370,689 discloses as a stapes replacement a passive middle ear prosthesis which comprises an elongated rod section one end of which is connected to the footplate of the stapes. An eyelet is provided at the other end of the rod section and is pushed over the free end of the long process of the incus. The motion of the stapes replacement which is driven by the long process of the incus is modified by a hitching member which is engaged by the stapedial tendon. For this reason the hitching member is slipped onto the rod section, the fit between the rod section and the inside surface of the hitching member being chosen such that the two parts can be moved relative to one another during implantation, whereas unwanted axial or rotational motion of the hitching member after implantation is precluded.

SUMMARY OF THE INVENTION

It is an object of this invention to provide for an arrangement which makes it possible to adjust the relative position of the two coupling halves of the coupling at the implantation site in situ as sensitively as possible in many degrees of freedom, the set relative position after implantation being reliably preserved in a simple manner with long term stability.

In conformity with the invention the arrangement includes a first coupling half of the coupling that has an outside contour with at least approximately the shape of a spherical cap which is adapted to be received in an inside contour of a second coupling half, with this inside contour being at least partially complementary to the said outside contour, wherein the coupling is adapted to be reversibly swiveled and/or turned against friction forces, but is essentially rigid with respect to dynamic forces which occur in the implanted state.

This arrangement provides an especially simple and nevertheless reliable manner that allows for moving the two coupling halves during implantation into a desired relative position. After implantation the mechanical vibrations which are induced in the first or second coupling half and which originate from the driver part are transmitted essentially rigidly to the other coupling half without the need for any additional operational step for this purpose. Proceeding from the stipulated known dynamic forces which must be transmitted in the implanted state by the coupling and from the higher forces which are typically applied by the surgeon in the course of implantation, the parameters which significantly influence the properties of the pair of the two coupling halves, such as the material, surface roughness (microgeometry) and fit (macrogeometry) are chosen such that especially the stick-slip effect and forces of friction between the coupling halves allow an easy, statically reversible adjustment of the coupling during implantation under the influence of the forces applied by the surgeon, whereas the coupling is rigid with respect to the dynamic forces to be transmitted in the implanted state.

The handling of the arrangement can be greatly simplified if the coupling is designed for reversible coupling and decoupling.

The second coupling half of the coupling can have at least two spring arms by which the first coupling half can be at least partially encompassed. The spring arms which can be connected by a material connection, for example soldering, brazing, welding, or the like, or which also can be made in one piece, can preferably contact the first coupling half with inwardly directed spring bias.

Furthermore, the second coupling half of the coupling can also have approximately a bell shape and can include especially several slots which extend essentially perpendicular to the peripheral direction and which extend to a face of the second coupling half facing the first coupling half. In this way, the first coupling half can be reliably held in the second coupling half At the same time, sufficient flexibility of the second coupling half for reversible coupling and decoupling is provided for.

Another advantageous embodiment of the invention has a second coupling which can be reversibly moved linearly and/or rotationally against friction forces, but is essentially rigid under the dynamic forces which occur in the implanted state. The first coupling half has an outside contour with an at least approximately cylindrical, preferably circularly cylindrical, shape which can be accommodated in an inside contour of the second coupling half, a contour which is at least partially complementary to the outside contour. The second coupling is preferably designed for reversible coupling and decoupling and can be positioned both between the coupling in which the first coupling half has approximately the shape of a spherical cap (first coupling) and the driver member and also between the first coupling and the coupling site. It is preferred that in the implanted state transmission of dynamic forces between the two coupling halves of the second coupling takes place essentially in the direction of the longitudinal axis of the first coupling half An especially simple structure arises when the second coupling half of the second coupling is made as a sleeve. The sleeve can have at least one slot which runs essentially in its longitudinal direction and which extends at least over a part of the sleeve length. Furthermore, to increase the flexibility, at least one slot can extend to a face of the sleeve facing the first coupling half.

If the slot extends over the entire length of the sleeve, the wall in the region of the two edges of the slot can be formed to point outwardly and the wall can define an insertion section into which the first coupling half can be inserted essentially perpendicular to its longitudinal axis.

At least one slot can end at least on one side in a relief opening which increases the elasticity of the second coupling half and its safety against damage, and which has a boundary line which connects the two sides of the slot, the relief opening transversely to the slot direction having a dimension which is greater than that of the slot.

The boundary line of at least one relief opening can connect the sides of the slot in an arc, especially essentially in a circular arc, or can be made in the form of a transversal slot which runs essentially perpendicular to the slot.

In another embodiment of the invention, at least one section of the wall of the sleeve of the second coupling is adapted to contact the first coupling half in an inwardly spring-biased manner. Furthermore, there can be at least two slots, and at least one section of a wall of the sleeve located between two adjacent slots is adapted to contact the first coupling half in an inwardly spring-biased manner. In doing so, it can be provided that at least two adjacent slots are connected to one another on the end side thereof, especially essentially in a U-shape manner, so that a spring tongue is formed.

To facilitate the coupling and decoupling process, the outside contour of the first coupling half of the second coupling in the area of its end facing the second coupling half can be provided with an insertion area which tapers in the direction towards the end.

For this purpose the inside contour of the second coupling half of at least one coupling in the area of its end facing the first coupling half can also be provided with an insertion area which widens in the direction towards the end. This applies both to the first and also the second coupling.

Moreover, at least a first and/or a second coupling half of at least one coupling can be advantageously connected integrally to the associated coupling element or the associated coupling rod.

The arrangement of the invention can be part of an active, partially implantable or fully implantable hearing system in which the output-side driver member is a vibratory member, especially a vibratory membrane, of an electromechanical hearing aid converter. The arrangement of the invention can however also be part of a passive hearing system, especially a partial or full middle ear prosthesis in which in the implanted state the eardrum is used as the output-side driver member.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIG. 1 is an enlarged view of an implanted hearing aid converter and a coupling arrangement with a coupling rod driven by the hearing aid converter, and a coupling element which is connected, on the one hand, via a coupling to the coupling rod, and on the other, is coupled to the ossicular chain;

FIGS. 4 and 5 are views of an embodiment of the invention in which the coupling between the coupling rod and the coupling element is made as a ball joint coupling;

FIG. 6 is a perspective view of a modified coupling element with an altered ball joint coupling;

FIGS. 7 to 11 are perspective views of modified coupling elements with two couplings, the first coupling being made as a ball joint coupling and the second coupling being made as a plug coupling;

FIG. 18 is a perspective view of a passive middle ear prosthesis with a ball joint coupling.

DETAILED DESCRIPTION OF THE INVENTION

Figure 2:
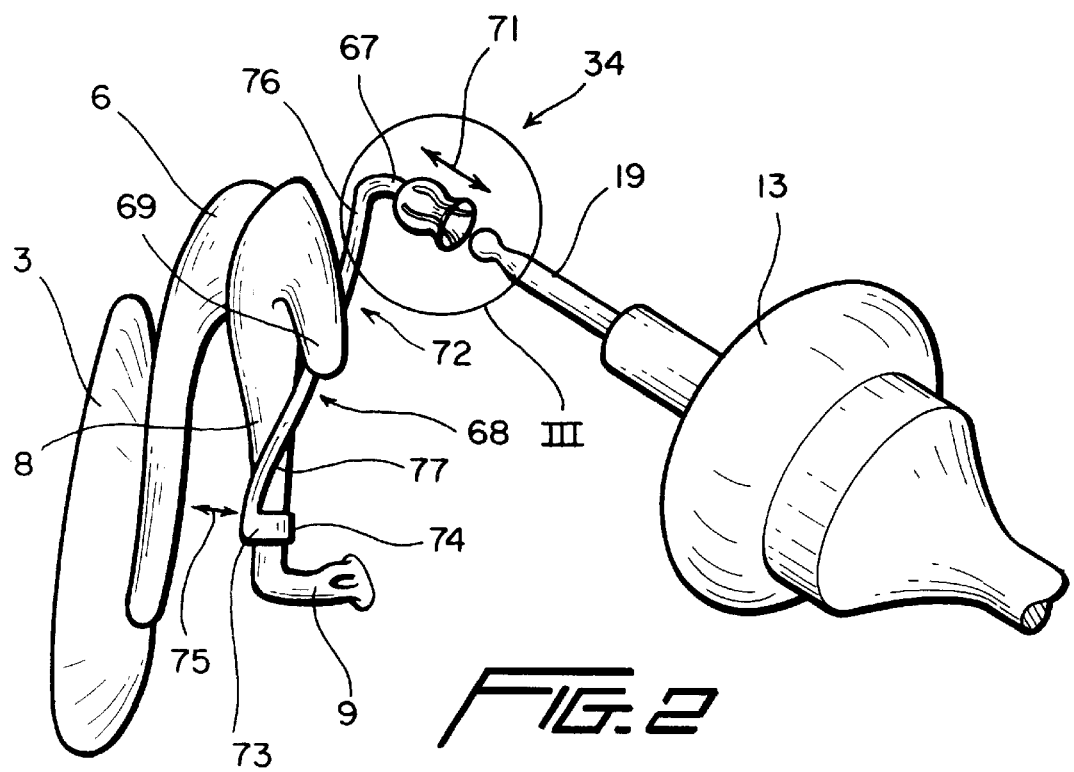
FIG. 2 shows, on a still larger scale, a perspective view of the hearing aid converter as shown in FIG. 1 which is coupled via a modified coupling arrangement to the body of the incus.

FIG. 1 shows part of a human skull bone 1 with the auditory canal 2, the middle ear space (tympanic cavity) 4 which is separated therefrom by the eardrum 3, and the ossicular chain 5 which is located in the tympanic cavity. The ossicular chain 5 includes the malleus 6, the incus 7 with the long process 8 of the incus, and the stapes 9 with the footplate 10 of the stapes. In an artificial mastoid cavity 12, an electromechanical hearing aid converter 13 is fixed by means of a positioning and fixing system 14. The hearing aid converter 13 can be built, for example, as a piezoconverter for vibratory stimulation of the ossicular chain especially in the manner known from U.S. Pat. No. 5,277,694 and it is a component of an at least partially implantable and preferably fully implantable hearing aid, for example a hearing aid of the type known from HNO 1997 Vol. 45, pp. 749–774.

A vibration transmission path in the form of a biocompatible, mechanically passive coupling arrangement 17 is provided for mechanically coupling an outputside driver member 15 of the hearing aid converter 13 to a preselected coupling site 16 on the ossicular chain 5, for example to the "smooth", body of the incus 7, from the mastoid side, wherein the output-side driver member 15 is shown only schematically in FIG. 1, can be excited to mechanical vibrations, and preferably may be a vibratory membrane of this converter. The coupling arrangement 17 is connected to the actively vibrational output-side driver member 15 and, in the implanted state, it contacts the coupling site 16 with the coupling end which is remote from the hearing aid converter 13. When an electrical voltage is applied to the hearing aid converter 13, the coupling arrangement 17 is caused by means of the output-side driver member 15 to execute vibratory oscillations in the axial direction of the coupling arrangement. As a result, the electrically converted audio signals which are picked up by an input-side converter (microphone) (not shown), after electronic amplification in an electronic module of the active hearing system, lead directly to mechanical deflections of the coupling arrangement 17. These deflections correspond to the acoustic information. The deflections of the coupling arrangement 17 are relayed to the ossicular chain 5 of the middle ear or to the stapes 9, the footplate 10 of the stapes or a membrane which is not shown and which closes the oval or round window or an artificial window in the cochlea, in the vestibulum or in the labyrinth (equilibrium organ). The deflections of the coupling arrangement therefore cause an audiological amplification effect for a corresponding design of the preprocessing electronic system.

The coupling arrangement 17 has a coupling rod 19 which is mechanically joined securely to the output-side driver member 15 and which, in the embodiment shown, has essentially over its entire length the shape of a straight cylinder. The coupling rod 19 extends in the implanted state from the mastoid cavity 12 into the tympanic cavity 4 preferably through a natural, if necessary artificially widened, bone opening (aditus ad antrum) 21 which is located in the rear wall 20 of the auditory canal. The coupling arrangement 17 furthermore includes a coupling element 22 which is connected via a coupling 23 to the end of the coupling rod 19 remote from the hearing aid converter 13 and is coupled to the coupling site 16 via a coupling end.

The schematically shown coupling 23 comprises two coupling halves, of which the first coupling half has an outside contour with at least approximately the shape of a spherical cap which can be accommodated in the inside contour of a second coupling half, a contour which is at least partially complementary to the outside contour. The first coupling half is formed, preferably integrally, on the free end of the coupling rod 19. The coupling 23 is made such that it can be reversibly swiveled and turned against friction forces by the surgeon during implantation but is essentially rigid for the dynamic forces which occur in the implanted state. Thus, sensitive matching of the relative position of the coupling rod 19 and the coupling element 22 to the circumstances of the implantation site in situ is possible, the relative position once set after implantation no longer being changed by the dynamic forces which then occur.

Figure 3:
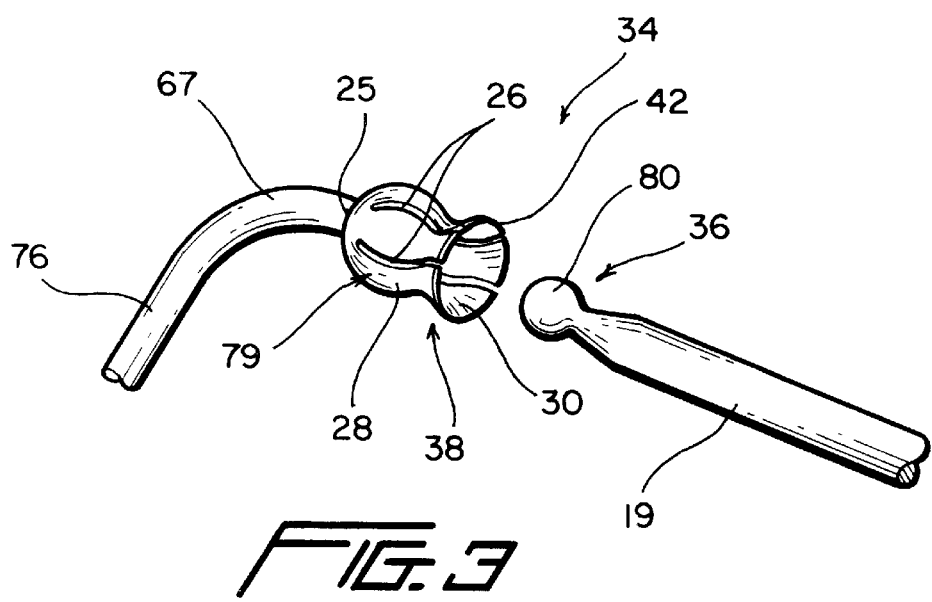
FIG. 3 is an enlarged perspective view of the area of FIG. 2 which is provided with a circle III.

FIGS. 2 and 3 show a coupling arrangement with a coupling 34 which is made as a ball joint coupling and with a first coupling half 36 which has a ball head 80 which can be inserted into a second coupling half 38 in the form of a ball receiver 79. The ball receiver 79 has an approximately bell-like shape with several slots 26 which extend from a face 42 towards the first coupling half 36 essentially perpendicular to the peripheral direction of the ball receiver 79. In this way spring arms 28 are formed which can spring reversibly to the outside during the coupling and decoupling process, an insertion area 30 which widens to the outside in the direction towards the face 42 facilitating the coupling of the ball head 80 to the ball receiver 79.

While the ball head 80 is made in one piece with the coupling rod 19, the ball receiver 79 merges via a connection piece 25 into a coupling rod-side end 67 of a coupling element 68. The coupling element 68 is made as a twin-arm lever with two arms 76 and 77 and is supported in the middle area thereof on the short process 69 of the incus. If the coupling rod-side end 67 of the arm 76 is forced to move according to the double arrow 71 by means of the coupling rod 19, the coupling element 68 swivels around a pivot 72 which is defined by the short process 69 of the incus. In this way, a coupling end 73 of the coupling element 68 which is located on the arm 77 and which engages the long process 8 of the incus via a spring clamp 74 or the like is moved in the direction of a double arrow 75. By correspondingly dimensioning the relative lengths of the arms 76 and 77 of the coupling element 68 a desired lever ratio can be set. The coupling 34 can not only be turned and swiveled in situ, it can also be coupled and decoupled at the implantation site, whereby the manageability of the device is greatly improved. After implantation, the set relative position of the coupling rod 19 and of the coupling element 68 is no longer changed by the dynamic forces which occur.

In a modified embodiment, as shown in FIGS. 4 and 5, there is a coupling 82 in the form of a ball joint coupling with a first coupling half which comprises a ball 103 which on the end of the coupling rod 19' facing away from the hearing aid converter 13 is joined integrally with the rod. The coupling element 83 can be an elastic clamp consisting of two spring arms 126 and 127, which are joined, preferably welded, to one another at 125. The spring arms, 126 and 127, form on the one hand a second coupling half in the form of a ball receiver 121 for the ball 103 of the coupling rod 19' and on the other hand a receiving opening 86 with a spreadable passage 87 for the target ossicle 8. To facilitate the coupling process between the two coupling halves of the coupling 82, the ball receiver 121 is provided with an insertion area 84 which widens in the direction to a face 90, the passage 87 for the target ossicle 8 being placed in a coupling end 100 of the coupling element 83 with a face 122 which is located essentially perpendicular to the face 90.

The coupling element 83 can be inserted by means of the coupling rod 19' through the opening 21 in the rear wall 20 of the auditory canal into the middle ear space 4 and can be positioned such that the spreadable passage 87 is aligned with the target ossicle, for example the long process 8 of the incus according to FIG. 4. Then the coupling element 83 is pressed down, and thus, swiveled in the direction of arrow 133 in FIG. 5 with reference to the coupling rod 19' until the target ossicle 8 lies in the receiving opening 86, with the passage 87 being widened. In this way reliable coupling to the target ossicle is achieved. In the implanted state, the coupling rod 19' executes vibrations essentially in the direction of the double arrow 88, the coupling 82 rigidly transmitting the vibrations.

A coupling element 117 which is shown in FIG. 6 comprises two undulating spring arms 119 which are welded together at 118 and which, on one side of the connection point 118, form a ball receiver 123 for the ball 103 of the coupling rod 19' and, on the other side of this connection point, form the spreadable passage 87 and the receiving opening 86 for the target ossicle. The coupling element 117 can be turned and swiveled relative to the coupling rod 19' according to the group of arrows 107 and it differs from the coupling element 83 as shown in FIGS. 4 and 5 essentially in that the ball receiver 123 as the second coupling half of a coupling 114 has no section corresponding to the insertion area 84 and accordingly cannot be reversibly coupled and decoupled. Furthermore, a face 128 which defines the passage 87 for the target ossicle, in contrast to the embodiment of FIGS. 4 and 5, is approximately parallel to the face 130 which delimits the second coupling half comprising the ball receiver 123. The coupling 114 also rigidly transmits the dynamic forces which occur in the implanted state.

In a modified embodiment of the arrangement of the invention as shown in FIGS. 7 and 8, a first and a second coupling are series connected, the coupling 114 of FIG. 6 being used as the first coupling. Instead of with the coupling rod 19', the ball 103 is, however, connected to a stem 142 of an intermediate element 164, which stem 142 is fixed via a widening section 158 to a sleeve 150 of a second coupling half 144 of the second coupling 146. A first coupling half 148 of the coupling 146 is formed a the free end of a coupling rod 19",the second end of which connected to the hearing aid converter and being caused thereby to vibrate. In order to be able to insert the free end of the coupling rod 19",facing away from the hearing aid converter 13 more easily into the sleeve 150 of the second coupling 146 which is made as a plug coupling, an insertion area 162 is provided at the free end of the coupling rod 19", which insertion area tapers towards the free end of the coupling rod 19" . The sleeve 150 in its wall 160 has several slots 152 which run essentially in the longitudinal direction of the sleeve 150 and which are approximately uniformly distributed around the circumference, and they end in front of the face 156 at the free end of the sleeve 150. A bridge 154 is formed between each pair of adjacent slots 152 which bridge is inwardly biased and contacts the first coupling half 148 with a stipulated contact force when the first coupling half 148 is inserted into the sleeve 150.

The series connection of two couplings in particular has the advantage that during implantation the arrangement at first can be divided into two modules by detaching the coupling 146, which modules can be handled separately and which again are connected to each other after the coupling element 117 has been coupled, by means of its receiving opening 86, to the target ossicle. The coupling 146 can be reversibly coupled and decoupled by the surgeon and in doing so can be shifted in situ in the longitudinal direction of the sleeve 150 and turned around the longitudinal axis of the sleeve 150, the design of the coupling 146 being such that the relative rotational and translatory position of the two coupling halves 144 and 148 which is adjusted by the surgeon remains stably preserved under the dynamic forces which occur in the implanted state, at least as long as a stipulated minimum insertion depth of the first coupling half 148 into the second coupling half 144 is maintained. Also, the other ball joint couplings and plug couplings described below can be moved in a statically reversible manner against friction forces during implantation, but rigidly transmit the lower dynamic forces which occur in the implanted state. FIGS. 9 and 10 show another embodiment of an arrangement in which, likewise, two series-connected couplings are used, a coupling 171 made as a plug coupling and a coupling 173 made in the form of a ball joint coupling. An intermediate element 166 differs from the intermediate element 164 of FIGS. 7 and 8 essentially only in that the second coupling half of the coupling 171 comprises a modified sleeve 168 which is provided with a single slot 170 which, proceeding from one face 204 on the free end of the sleeve 168, extends in the longitudinal direction of the sleeve and terminates in an essentially round relief opening 172 which joins the two sides 174 of the slot. The plug coupling 171 is designed such that the first coupling half 148 which is provided on the coupling rod 19″,is always inserted into a receiver 192 of the sleeve 168 until the free end of the first coupling half 148 comes to rest against a depth stop 206 within the sleeve 168. Optical inspection of the plug process is possible through the slot 170.

A coupling element 176 is made in one piece and comprises, as the second coupling half of the coupling 173, a ball receiver 184 which is formed by two opposite spring arms 186 and 188 which both extend to a coupling-side face 185 of the coupling element 176. To increase the flexibility of the spring arm 188 the latter is extended in a U-shape in the direction towards a receiving opening 182 for the target ossicle. A leg 193 opposite a spring arm 189 is connected via a crosspiece 191 to the spring arm 186, with a crosspiece 187, which is provided between the leg 193 and the spring arm 189, being designed such that its outside surface facing away from the ball receiver 184 together with an inner surface of a spring clip 180 forms the receiving opening 182. The spring clip 180 is formed on the side of the crosspiece 191 opposite the spring arm 186 to the crosspiece and at first runs, as a thin-walled extension of the spring clip 186, substantially parallel to the leg 193 and then merges into an arc-shaped segment 181. The free end of the segment 181 ends essentially at the same height as a side surface 189 of the spring arm 188 so that the target ossicle is inserted substantially perpendicular with reference to the side surface 189 into the receiving opening 182 which is provided on the coupling end 178 of the coupling element 176. The side surface 189 is aligned substantially perpendicular with reference to a plane containing the face 185. An opening 190 is made in each of the spring arms 186 and 188 such that the two openings have a common longitudinal axis which extends through the center of the ball 103. In this way, the faces of the openings 190 facing the ball 103, each form a defined contact surface for the ball 103, which contact surfaces can be made in the manner of a ball socket. Preferably, the entire coupling element 176 is made of titanium or a titanium alloy.

Figure 11:
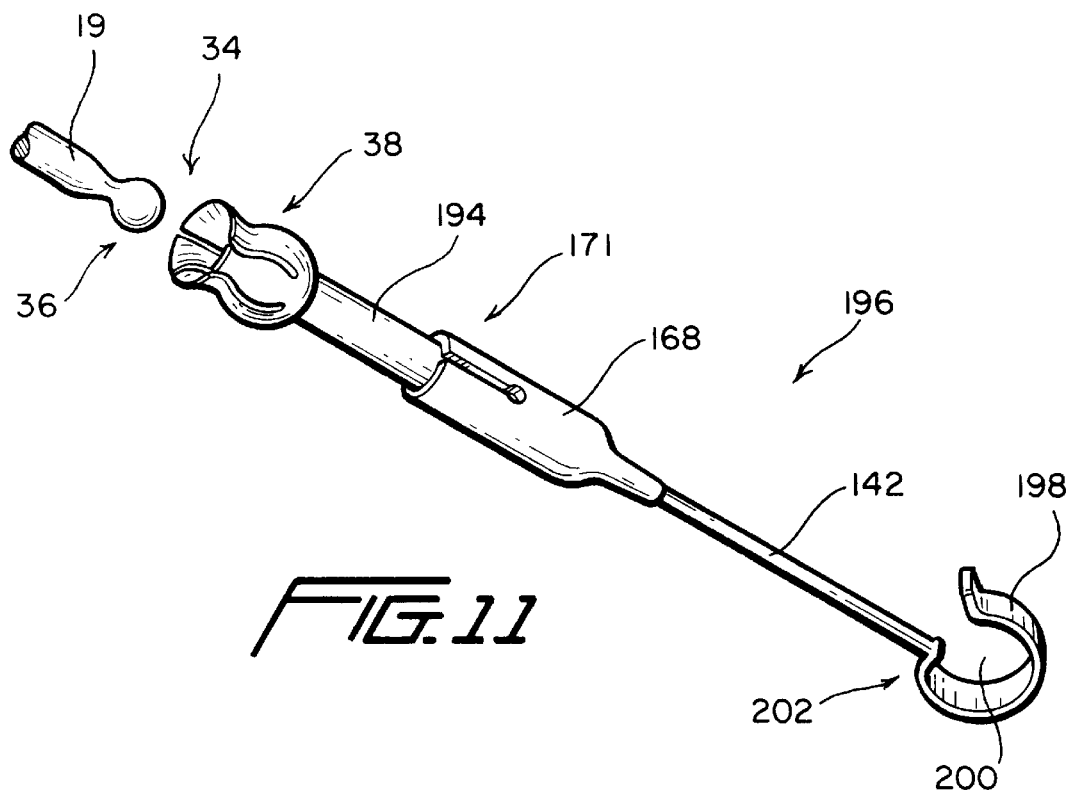

FIG. 11 shows an arrangement in which the ball joint coupling is the coupling 34 as shown in FIGS. 2 and 3 and the plug coupling is the coupling 171 of FIGS. 9 and 10, the second coupling half 38 of the coupling 34 being connected to a stem 194 the free end of which defines the first coupling half of the coupling 171. In contrast to the embodiment shown in FIGS. 9 and 10, the stem 142, which is connected to the sleeve 168, however, does not terminate in the ball 103, but merges into a coupling end 202 for the target ossicle. The coupling end 202 comprises a band loop 198 which forms a receiving opening 200 for the target ossicle and which can be placed for example around the long process 8 of the incus. The sleeve 168 and the stem 142 are made in one piece and the material is preferably titanium or a titanium alloy, whereas the band loop 198 is made especially of gold or a gold alloy.

Figure 12:
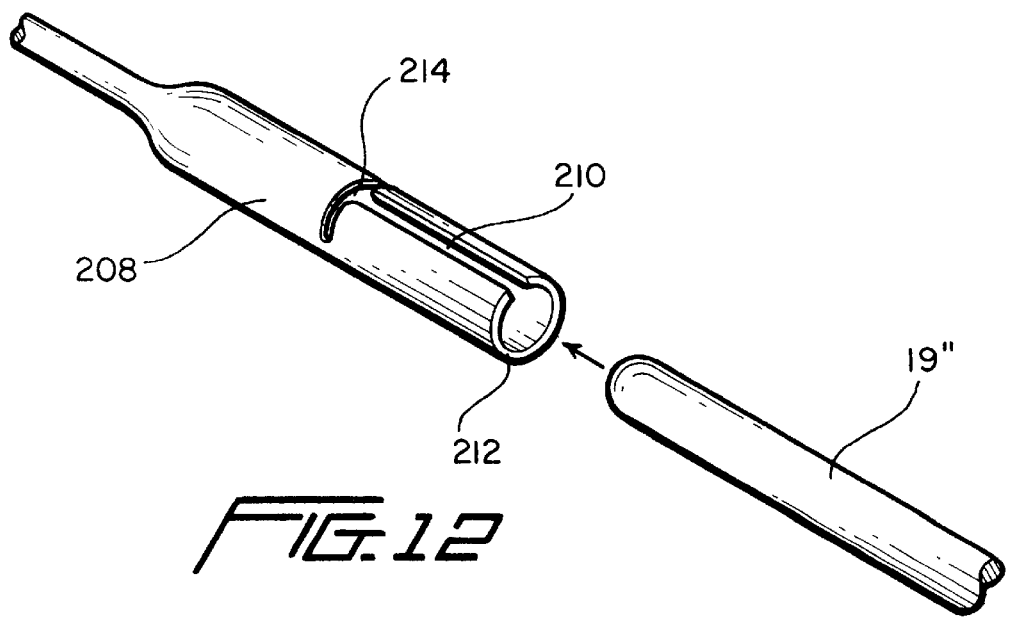
FIGS. 12 to 15 are perspective views of additional modified plug couplings.

The plug coupling which is shown in FIG. 12 differs from the coupling 171 as shown in FIGS. 9 and 10 mainly in that a slot 210, which is made in the sleeve 208 on its end facing away from a face 212, does not end in a round relief opening corresponding to the relief opening 172 of the sleeve 168, but ends in a transverse slot 214 which is made essentially perpendicular to the slot 210.

Figure 13:
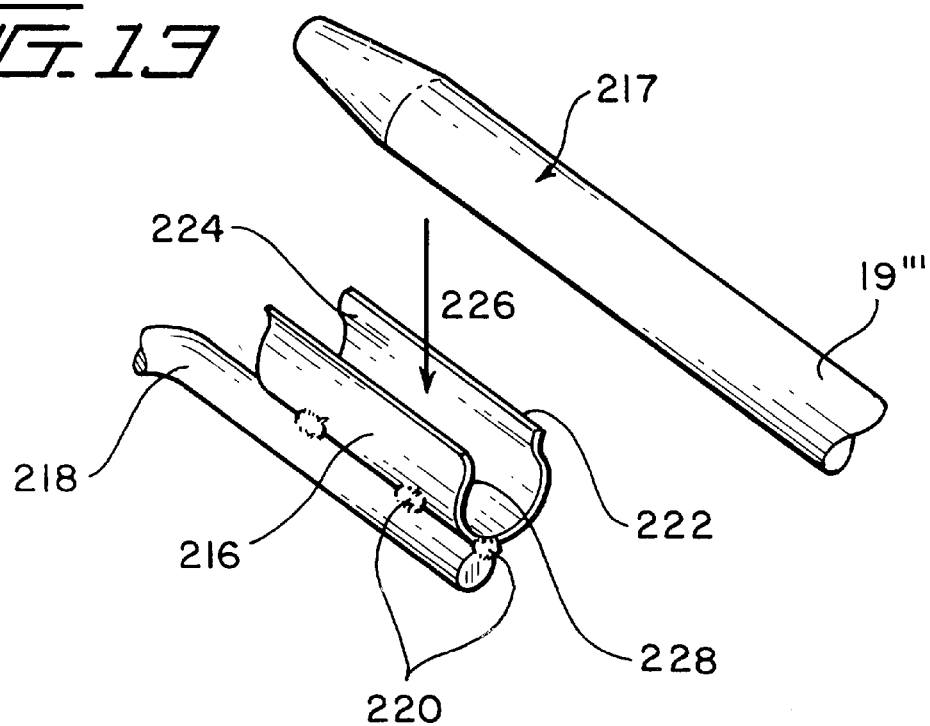

Other modified plug couplings are shown in FIGS. 13 to 17. Thus, in a plug coupling as shown in FIG. 13 a first coupling half 217, which is formed at the free end of a coupling rod 19″, is inserted in the direction of arrow 226, essentially perpendicular to the longitudinal axis of a second coupling half which is made as a sleeve 216. For this purpose the sleeve 216 is provided with a slot which extends over the full length of the sleeve, wherein a wall 228 of the sleeve 216, in the area of both sides 222 of the slot, is formed to point outwardly so that an insertion area 224 results. When the first coupling half 217 is coupled to sleeve 216, an outer wall of the first coupling half 217 cooperates with the insertion area 224 and facilitates spring widening of the sleeve 216. The sleeve 216 is connected, especially welded, brazed or soldered, on its outer side which is substantially diametrically opposite the slot, to a stem 218 of the coupling arrangement via connection points 220.

Figure 14:
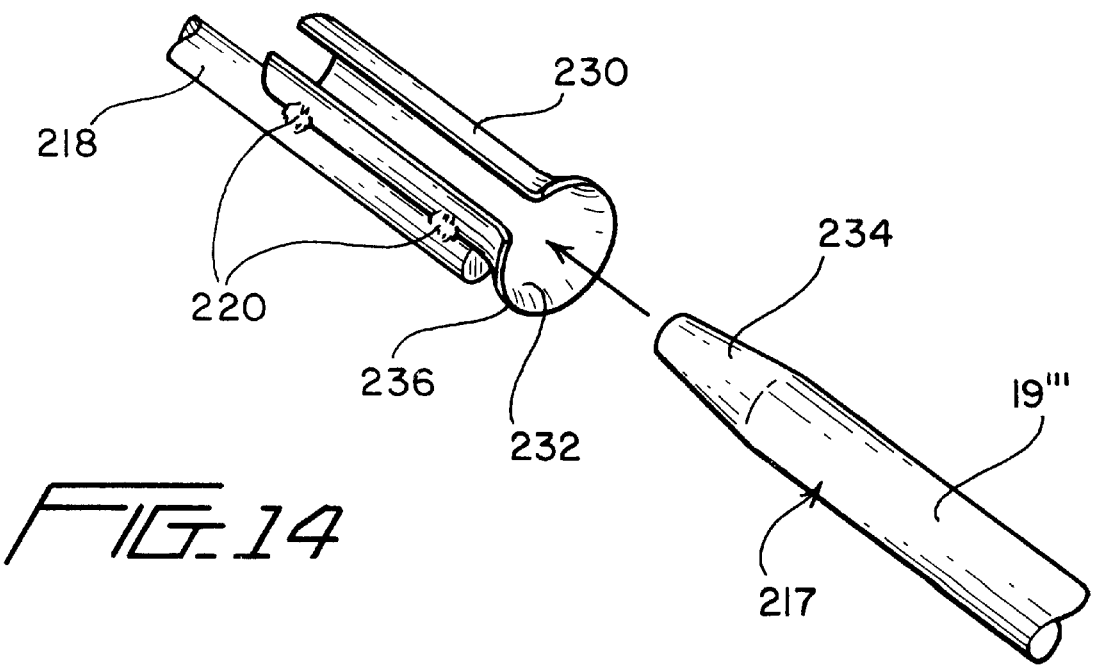

The plug coupling which is shown in FIG. 14 also comprises as the second coupling half a sleeve 230 with a continuous slot, but in contrast to the sleeve 216 as shown in FIG. 13, an outwardly widening insertion area 232 is provided at a face 236 of a free end of the sleeve 230, and the wall of the sleeve 230 otherwise has an approximately circular cylindrical shape. The coupling of the first coupling half 217 to the sleeve 230 takes place, essentially, in the longitudinal direction of the sleeve, the insertion area 232 of the sleeve 230 interacting with a conically tapering insertion area 234 which is provided on the free end of the first coupling half 217 and which facilitates the spring widening of the sleeve 230.

Figure 15:
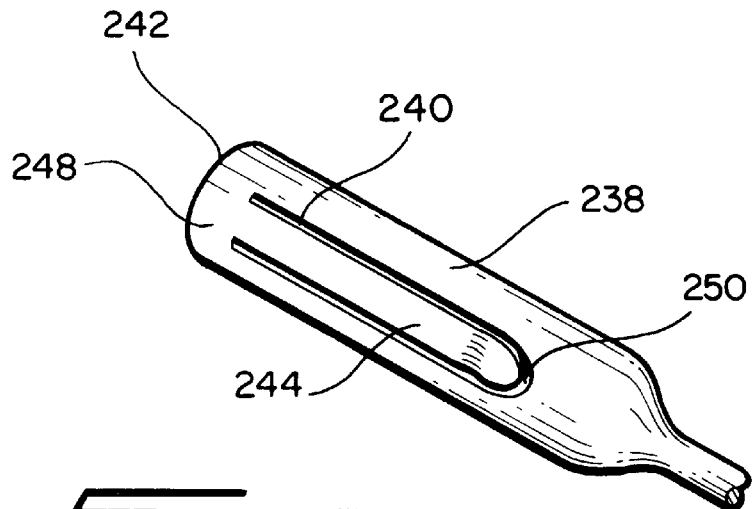
Figure 16:
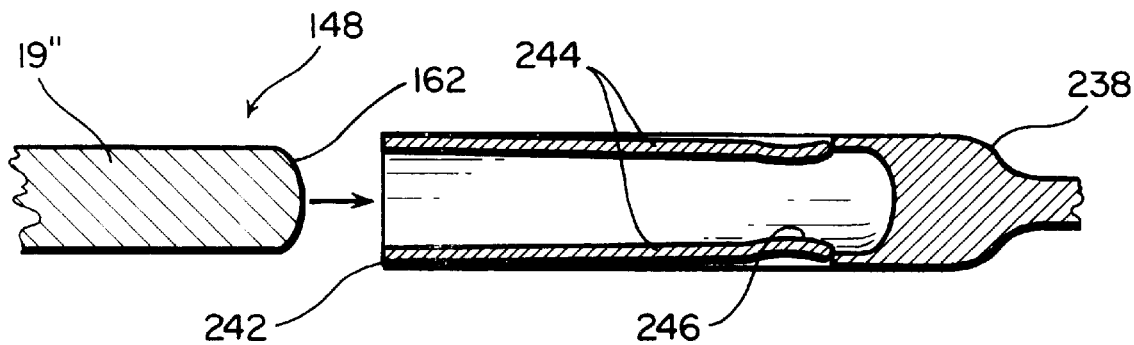
FIGS. 16 and 17 are cross-sectional views of the plug coupling of FIG. 15.
Figure 17:
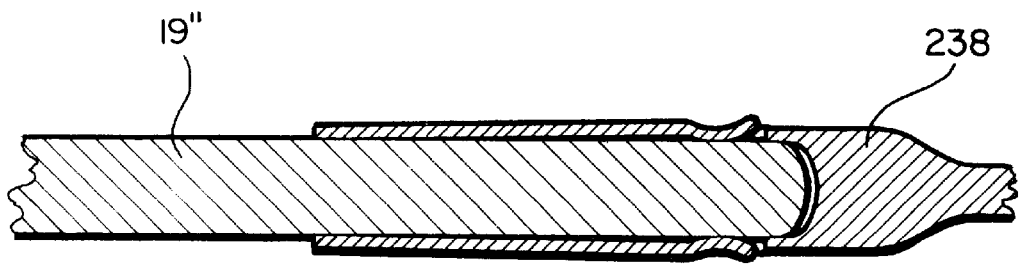

FIGS. 15 to 17 show another modified plug coupling which differs from the coupling 146 shown in FIGS. 7 and 8, essentially, only by the configuration of slots 240 in a wall 248 of the second coupling half, which is made as a sleeve 238. Like the slots 152 in the sleeve 150 as shown in FIGS. 7 and 8, the slots 240 in the sleeve 238 also run, essentially, in the longitudinal direction of the sleeve and terminate in front of a face 242 of the sleeve 238. But, overall, four slots 240 are made in the wall 248 of the sleeve 238 such that each two slots 240 are more closely spaced from each other and are interconnected on their end facing away from the face 242 via an essentially U-shaped slot segment 250. Thereby two diametrically opposite spring tongues 244 are formed which are inwardly spring-biased, wherein a free end of the tongues 244 projects in an arc shape to the inside and can be placed against the outside surface of the first coupling half 148 via a contact surface 246.

FIG. 18 shows an implanted passive hearing system in which the eardrum 3 is used as the output-side driver member which can be excited to mechanical vibrations. The eardrum 3 is contacted by a head 136 of a T.O.R.P. (total ossicular replacement prosthesis) 135, the head 136 having a rounded surface. The head 136 is adjoined by a coupling rod 139, which can be joined integrally to the head 136 and which has a free end which is connected to the free end of a coupling element 137 via a coupling 140 which is made as a ball joint coupling. A coupling end 138 of the coupling element 137 facing away from the coupling 140 is coupled to the head 141 of the stapes. The coupling 140 during implantation allows reversible static swiveling and turning of the coupling element 137 and the coupling rod 139 with reference to one another, but rigidly transfers the dynamic forces which are delivered to the coupling in the implanted state by the eardrum 3. Preferably, the head 136, the coupling rod 139 and the coupling element 137 are made of an implantable metallic or ceramic material.

In general, all known biocompatible metals and their alloys can be used as the materials for the coupling rod, the coupling element, the coupling and the intermediate element which is inserted, if necessary, between the two couplings, particularly implantable titanium, especially pure titanium with a purity >99.6%. In addition, among others, platinum, niobium, or tantalum or alloys of titanium, platinum, niobium or tantalum are suited. Optionally, the coupling rod or other of the indicated components can, however, also be made of an implantable ceramic material, especially aluminum oxide. But also, long-term implantable plastics can be provided, such as, among others, cross-linked silicones, polyurethanes, PTFE, FEP, polycarbonates and the like, which can be optionally fiber reinforced, especially carbon fiber reinforced. However, at least a section of the coupling element, which section in the implanted state contacts the coupling site on the ossicular chain, the is footplate of the stapes or a membrane which closes the round window or an artificial window in the cochlea, in the vestibulum or in the labyrinth (equilibrium organ), is designed for vibratory input to the coupling site, and thus, has only low entropy elasticity. This section of the coupling element contacting the coupling site is made preferably of one of the indicated metallic or ceramic materials or is made of gold or a gold alloy.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications.

What is claimed is:

1. A coupling system for use with an output-side driver of an implantable hearing system, said coupling system having a first coupling with a coupling rod and a coupling element, said first coupling comprising:
    a first coupling half with an approximately spherical outside contour; and
    a second coupling half that is adapted to receive said spherical outside contour of said first coupling half and having an inside contour that is complementary to said spherical outside contour of said first coupling half, wherein said coupling is adapted to be substantially rigid with respect to dynamic forces which occur when said hearing system is implanted and adapted to at least one of swivel and turn against friction forces when said hearing system is being at least one of implanted and adjusted.

2. The coupling system of claim 1, wherein said first coupling is adapted to reversibly couple and decouple.

3. The coupling system of claim 1, wherein said second coupling half comprises at least two spring arms which are adapted to at least partially encompass said first coupling half.

4. The coupling system of claim 3, wherein said at least two spring arms are elastically pretensioned toward the inside of said second coupling half such that said spring arms are adapted to squeeze said first coupling half when said first coupling half is coupled with said second coupling half.

5. The coupling system of claim 1, wherein said second coupling half is approximately bell-shaped.

6. The coupling system of claim 5, wherein said second coupling half includes a plurality of slots extending from a face of said second coupling half.

7. The coupling system of claim 1, further comprising a second coupling having:
    a first coupling half having an approximately cylindrical outside contour; and
    a second coupling half that is adapted to receive said outside contour of said first coupling half and having an inside contour that is at least partly complementary to said outside contour of said first coupling half.

8. The coupling system of claim 7, wherein said outside contour of said first coupling half of said second coupling has a circular cylindrical shape.

9. The coupling system of claim 7, wherein said second coupling half of said second coupling is a sleeve.

10. The coupling system of claim 9, wherein said sleeve has at least one slot that runs axially along said sleeve.

11. The coupling system of claim 10, wherein at least one slot extends to a face of said sleeve.

12. The coupling system of claim 10, wherein a slot extends along the entire length of said sleeve.

13. The coupling system of claim 10, wherein at least one slot does not extend to a face of said sleeve.

14. The coupling system of claim 10, wherein at least one slot ends in a relief opening having a boundary that connects two sides of said at least one slot, wherein said relief opening has a transverse dimension that is greater than the transverse width of said at least one slot.

15. The coupling system of claim 14, wherein said boundary is arc-shaped.

16. The coupling system of claim 15, wherein said boundary is circular.

17. The coupling system of claim 14, wherein said relief opening extends perpendicularly with respect to said at least one slot.

18. The coupling system of claim 9, wherein at least one section of a wall of said sleeve is elastically pretensioned toward the inside of said sleeve.

19. The coupling system of claim 9, wherein said sleeve includes at least two adjacent slots defining a wall that is elastically pretensioned toward the inside of said sleeve.

20. The coupling system of claim 19, wherein said at least two adjacent slots are connected at their ends by a U-shaped slot.

21. The coupling system of claim 8, wherein said sleeve has an insertion area that tapers toward an end face of said sleeve.

22. The coupling system of claim 8, wherein said second coupling is adapted to transmit dynamic forces between said first and second coupling halves in an axial direction when implanted.

23. The coupling system of claim 7, wherein one of said second coupling halves has an insertion area for said corresponding first coupling half that widens toward the end face of the second coupling half.

24. The coupling system of claim 7, wherein at least one of said first and second halves of one of said first and second couplings is connected integrally to a corresponding one of said coupling element and coupling rod.

\* \* \* \* \*